United States Patent [19]

Berkcan

[11] Patent Number: 5,324,933

[45] Date of Patent: Jun. 28, 1994

[54] HIGH ACCURACY AND HIGH SENSITIVITY ENVIRONMENTAL FIBER OPTIC SENSOR WITH CORRUGATIONS

[75] Inventor: Ertugrul Berkcan, Niskayuna, N.Y.

[73] Assignee: General Electric Company, Schenectady, N.Y.

[21] Appl. No.: 79,763

[22] Filed: Jun. 21, 1993

[51] Int. Cl.$^5$ .............................................. H01J 5/16
[52] U.S. Cl. ................... 250/227.23; 385/12; 250/227.18
[58] Field of Search ................ 250/227.18, 227.14, 250/227.16, 227.23, 227.21; 385/12, 13

[56] References Cited

U.S. PATENT DOCUMENTS

| | | | |
|---|---|---|---|
| 4,560,248 | 12/1985 | Cramp et al. | 385/12 |
| 4,795,226 | 1/1989 | Bennion et al. | 385/12 |
| 4,815,843 | 3/1989 | Tiefenthaler et al. | 356/128 |
| 4,834,496 | 5/1989 | Blyler, Jr. et al. | 250/227.18 |
| 5,007,705 | 4/1991 | Morey et al. | 385/12 |
| 5,138,153 | 8/1992 | Gergely et al. | 250/227.21 |

OTHER PUBLICATIONS

Whalen et al., "Wavelength-Tunable Single-Made Fibre Grating Reflector", Electronics Letters, vol. 22, pp. 1307-1308 (1986).
"High-Reflectivity Monomode-Fibre Grating Filters", by I. Bennion, et al, Electronic Letters, vol. 22, No. 6, Mar. 1986.
"Fiber Bragg Grating Chemical Sensor", by G. Meltz, et al, SPIE, vol. 1587, 1991.
"Photocharge Process", by J. Gaynor, et al, Photographic Science and Engineering, vol. 11, No. 3, 1967.
"Deformation Recording Media", Encyclopedia of Chemical Technology, vol. 7, 3rd Edition, pp. 448–461, 1979.
"A Single-Mode Fiber Evanescent Grating Reflector", by W. V. Sorin, et al, Journal of Lightwave Technology, vol. LT-3, No. 5, Oct. 1985.
"Flory-Huggins Theory" [163,164], ISBN 0-387-507-77-9 Polymers, 1990.
"Narrow-band Bragg Reflectors in Optical Fibers", B. S. Kawasaki, et al, Optics Letters, vol. 3, No. 2, Aug. 1978.
"Formation of Bragg gratings in optical fibers by a transverse holoraphic method", G. Meltz, et al, Optics Letters, vol. 14, No. 15, Aug. 1989.
"Grating-fiber Coupler as a High-Resolution Spectrometer", by P. St. J. Russell et al, vol. 10, No. 6, Jun. 1985, Optics Letter.

*Primary Examiner*—Michael Messinger
*Attorney, Agent, or Firm*—Ann M. Kratz; Marvin Snyder

[57] ABSTRACT

An apparatus for detecting a measurand includes a fiber field access block having a clad fiber positioned in the fiber field access block such that a portion of the fiber is exposed to an outer surface and any cladding on that portion of the clad fiber is thinner than required to prevent an evanescent wave from escaping the clad fiber. A measurand sensitive layer is provided over the outer surface. A grating is present in either the measurand sensitive layer or the fiber. An optical source and an optical detection component are coupled to the clad fiber. The optical detection component measures shifts in output signals resulting from presence of the measurand in the environment of the fiber field access block caused by changing Bragg conditions which result from swelling of the measurand sensitive layer. The concentration of the measurand can be determined from the detected shifts.

29 Claims, 6 Drawing Sheets

HIGH ACCURACY AND HIGH SENSITIVITY ENVIRONMENTAL FIBER OPTIC SENSOR WITH CORRUGATIONS

CROSS-REFERENCE TO RELATED APPLICATION

This application is related to the following co-pending application which is commonly assigned and is incorporated herein by reference: Berkcan, "Fiber Field Access Block Evanescent Wave Sensors", Ser. No. 079,764, filed concurrently herewith.

BACKGROUND OF THE INVENTION

1. Field of the Invention

This invention relates generally to sensors, and, more particularly, to sensors of various analytes fabricated by positioning on a fiber field access block a corrugated measurand sensitive layer whose properties ar changed as a result of interactions with the environment.

2. Description of the Related Art

One conventional device for detecting the presence of analytes is an extrinsic polymer swelling sensor that uses reflections form a surface which is moved by the swelling of the polymer to provide an indication of the concentration of analytes. This type of sensor cannot be protected from the effects of temperature and is vulnerable to vibrations, pressure changes, and contaminants that may exist in the analyte.

Several other fiber optic chemical sensors rely on conventional spectroscopic instrumentation. In these cases the detector is usually a photomultiplier tube or a photodiode. The sources are usually a tungsten-halogen lamp, a xenon arc lamp, or an argon ion laser. These types of sensors require sophisticated, miniaturized demodulation equipment.

Other attempts have been made to use sensors to exploit properties of fiber optic media to transport light between a sample and the light source or detector. These techniques use light wavelengths in the blue or ultraviolet range in order to be sensitive to the spectral characteristics of the species formed by reaction of an indicator reagent with the analyte. These wavelengths require special lasers and are not transmitted well due to the absorption properties of the fibers. Additionally, the sensor stability is generally limited by the indicator. Since the detection mechanism requires photoexcitation, photodecomposition becomes an additional problem. Moreover, the associated dyes are usually unstable.

When light passes through a gradient in the index of refraction, such as may be created by an acoustical wave acting on the medium in which light is travelling, the light is diffracted. Structures with periodic distribution of the index of refraction are useful for providing phase matching between light modes that travel with different propagation velocities. This type of periodic distribution of the index of refraction is referred to as a grating structure.

SUMMARY OF THE INVENTION

An object of the invention is to provide a system for accurately detecting the presence and concentration of analytes in environmental matrices.

Another object of the invention is to provide a totally intrinsic sensor and thereby avoid the need to seal any optical cavity.

Another object of the invention is to provide a method for sensing analytes using a broadband source, thus allowing use of commercially obtainable light emitting diodes.

Another object of the invention is to allow measurement of different analyte parameters by multiplexing multiple sensors.

The invention achieves the above objects by depositing a rectangular waveguide on a fiber field access block and measuring Bragg condition modifications (which result from the fact that swelling of the waveguide changes the wavelength of the light that is reflected) to optically detect changes in the rectangular waveguide as a result of interactions with the measurand. The term "measurand" is intended to encompass features which are capable of measurement using the present invention. Examples include analytes as well as physical properties such as temperature and pressure.

In this case, coupling to the guided wave in the backward direction can be obtained by using a corrugated layer (thus obtaining a grating structure) on top of a fiber field access block or by using a corrugated fiber in the fiber field access block. To efficiently couple light into the backward direction, the spatial period $\Lambda$ of the grating structure is preferably in a particular relationship with the wavelength of the light traveling in the optical fiber. This relationship is given by $\Lambda = \lambda_0 / 2n_{eff}$ where $\lambda_0$ is the speed of light in a vacuum, and $n_{eff}$ is the effective refractive index of the guided mode and provides a measure for the effective speed with which light is guided through the fiber optic medium, as described in W. V. Sorin & H. J. Shaw, "Single-Mode Fiber Evanescent Grating Reflector," J. of Lightwave Technology, vol. LT-3, No. 5, October 1985, pp. 1041–1043, and M. S. Whalen et al., "Wavelength-Tunable Single-mode fibre Grating Reflector," Electronics Letters 22, 1307–08. This relationship is referred to as the Bragg condition. Higher order conditions can result in slightly different relationships (such as $\Lambda = n\lambda_0 / 2n_{eff}$) and radiated modes rather than guided modes in the fiber.

Briefly, in accordance with a preferred embodiment of the invention, an apparatus for detecting the presence of a measurand comprises a fiber field access block, a measurand sensitive layer, which may be corrugated, over the fiber field access block, and means for detecting changes in the measurand sensitive layer caused by interaction with the measurand. The fiber field access block has a clad fiber, which is corrugated if the measurand sensitive layer is not corrugated, positioned such that a portion of the clad fiber is exposed to the measurand sensitive layer and the cladding, if any, on that portion of the clad fiber is of insufficient thickness to prevent an evanescent wave from escaping the clad fiber.

In accordance with another preferred embodiment of the present invention, a method for detecting analytes comprises providing a fiber field access block having a clad fiber positioned in the fiber field access block such that a portion of the clad fiber is exposed to an outer surface of the fiber field access block. A measurand sensitive layer, which may be corrugated, is provided over the outer surface of the fiber field access block. If the measurand sensitive layer is not corrugated, then the clad fiber should be corrugated. The fiber field access block is positioned in an environmental matrix. An optical signal is provided through the clad fiber. The optical signal produced from the clad fiber is then measured.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings, where like numerals represent like components, in which:

DETAILED DESCRIPTION OF A PREFERRED EMBODIMENT OF THE INVENTION

Figure 1:
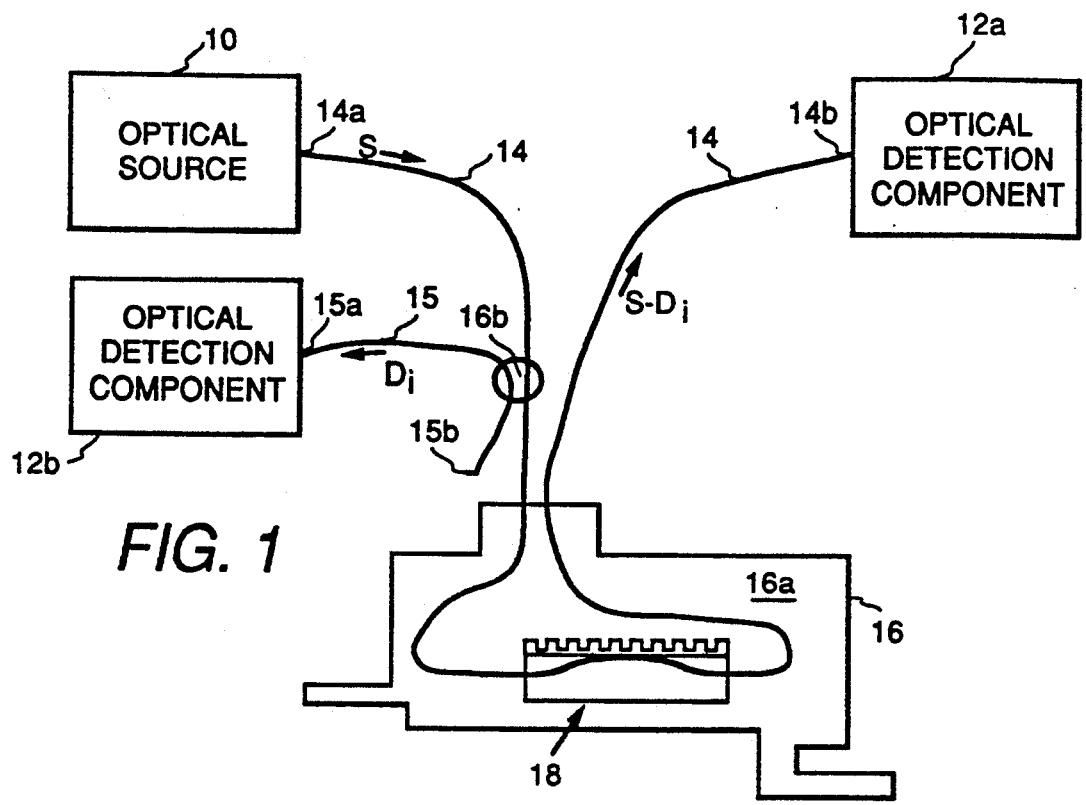
FIG. 1 is a schematic view of the invention including a fiber optic sensor in an environmental matrix, an optical source, and optical detection components.

FIG. 1 is a schematic view of the invention including a fiber optic sensor 18 in an environmental matrix 16a contained in a test chamber 16, a fiber 14, an optical source 10, and optical detection components 12a and 12b. Light (S) from optical source 10 enters fiber 14 at a fiber entrance end 14a. Optical source 10 can comprise any appropriate light source, including, for example, a light emitting diode.

The portion of the light $(S-D_i)$ which travels in the fiber through the fiber optic sensor can be detected at an exit end 14b by detection component 12a. The portion of the light which is reflected $(D_i)$ can be detected with detection component 12b by using a directional coupler 16b for allowing back-scattered light from the sensor to be coupled away from the source along fiber 15 to one end 15a of fiber 15. In the preferred embodiment, the other end 15b of fiber 15 is either crushed or coated with an index matching gel, for example, so that no light is reflected from end 15b to end 15a. Each detection component includes a physical detector, such as a photodiode, and can additionally include demodulation components. The relevant measurement information can be obtained by either of the two detection components, so only one of the two detection components shown is required for the invention.

Environmental matrix 16a can be any type of environment where testing is desired, including, for example, air, water, and soil. Potential analytes which can be detected include organic solvents, chlorinated hydrocarbons such as TCE (trichloroethylene), gasoline and fuel components, heavy metals such as Hg vapor, PCBs (polychlorinated biphenyls), and gases such as $H_2$ and $O_2$.

Figure 2A:
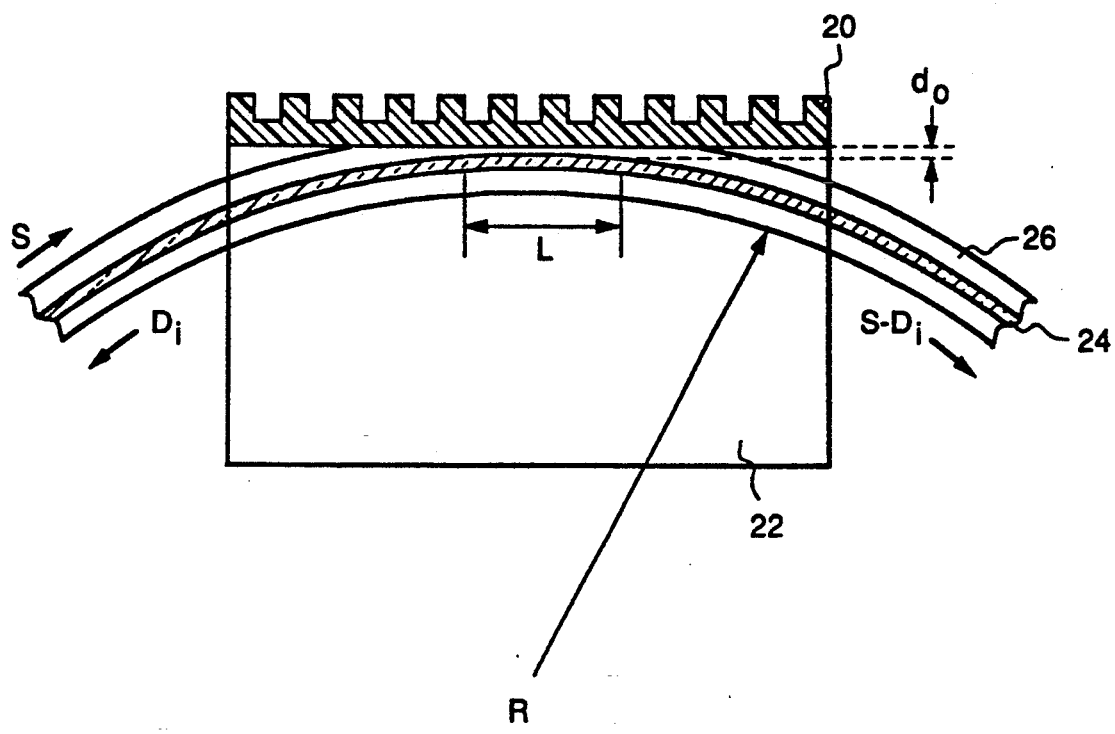
FIG. 2(a) is a sectional side view of a fiber optic sensor of the invention including a fiber field access block and a corrugated measurand sensitive layer.
Figure 2B:
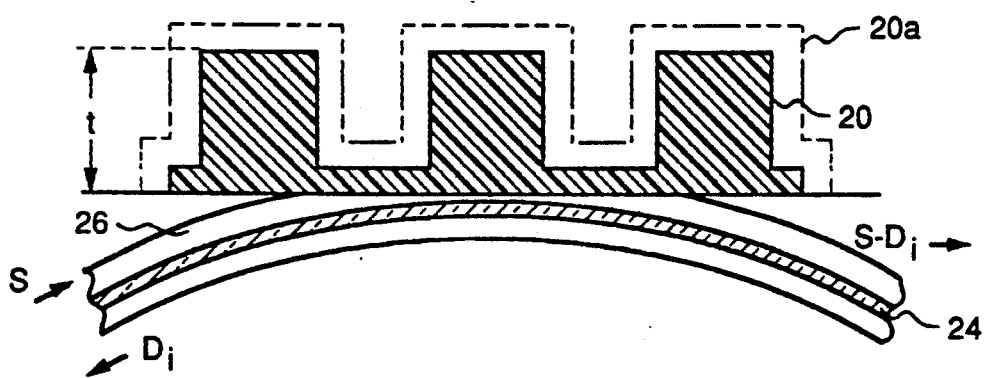
FIG. 2(b) is a sectional side view illustrating swelling of the corrugated measurand sensitive layer shown in FIG. 2(a)

FIG. 2(a) is a sectional side view of a fiber optic sensor of the invention including a fiber field access block 22 and a corrugated measurand sensitive layer 20. FIG. 2(b) is a sectional side view illustrating by phantom line 20a the expanded layer 20 after swelling which results when the corrugated measurand sensitive layer shown in FIG. 2(a) is in the presence of a measurand. The absorption of an analyte into the measurand sensitive layer causes both swelling in the layer (so its physical thickness t increases) and alterations in the layer's index of refraction n (so its optical thickness, $o = tn$, changes). Physical properties such as temperature and pressure also result in changing physical and optical thicknesses. Fiber 14 has a core 24 comprising, for example, fused silica or fused silica with germanium covered by cladding 26 comprising, for example, a polymer or fused silica.

A fiber field access block, such as block 22, is a block with a groove and a fiber 14, having a core 24 covered by cladding 26, inserted in the groove and polished such that a portion of fiber cladding 26 is removed from fiber 14 in an outer surface of the fiber field access block. The cladding, if any, on portion L of the fiber is thinner than the minimum thickness $d_o$ normally required to prevent the evanescent wave from escaping the fiber. Fiber field access blocks have part of the fiber cladding removed by controlled mechanical polishing along one side of the fiber. The fiber is first placed or mounted in a curved groove of radius R in a fused silica substrate, and bonded thereto. The substrate and fiber are then ground and polished until the desired cladding thickness (typically 1-2 μm) remains. This reduced cladding of the fiber allows the evanescent field to interact with the corrugated measurand sensitive layer. Fiber field access blocks are commercially available from Sifam Ltd., Torquay, Devon, United Kingdom and Canadian Instrumentation and Research Ltd. (CIR), Burlington, Ontario, Canada. The fiber supports at least one guided mode (i.e., allows at least one certain wavelength of light to be totally internally reflected and carried from one end of the fiber to the other end).

In one embodiment, measurand sensitive layer 20 forms a grating on top of the cylindrical waveguide formed by fiber 14. In an embodiment which is especially useful for the detection of fuel and organic solvents, measurand sensitive layer 20 is a crosslinked polymer chosen on the basis of its index of refraction as well as its absorption properties. The mechanism of swelling is altered by using polymeric layers of different crosslinking densities. The swelling can thus be adjusted between Fickian and Case-II behavior as discussed below. This behavior is different for different analytes, and thus significantly improves the specificity of the sensor.

The polymer material in this embodiment is chosen for its solubility in the presence of the analyte of interest before the crosslinking. The crosslinking density is then chosen to promote swelling and to prevent dissolution due to the permanent chemical interconnections resulting from crosslinking.

In one example, an epoxy resin is used as the polymer. One hundred parts of diglycidyl ether of bisphenol A and ten parts of diethylene triamene are mixed at mixing temperature Tm (typically 50° C.–70° C.). The mixture is then allowed to cure at temperature Tc (typically about 25° C.) for a period of time (typically 2–3 days). This procedure results in crosslinked glassy polymers. Different choices of Tm and Tc lead to different degrees of crosslinking resulting in different rates of penetration of analytes into the polymer.

A second example uses, as the polymer, gelatin mixed with ammonium dichromate at room temperatures and baked at temperature Tc. Again, the choice of Tc provides different degrees of crosslinking. Several other examples include poly(chloroprene) solvent cast and baked at temperature Tc and styrene-butadiene-styrene co-polymer solvent cast and baked at temperature Tc.

Preferably an adhesion promoter (not shown), such as, for example, a trimethoxsilane, is applied to the surface of the fiber field access block prior to application of polymer layer 20 by, for example, spin coating. The choice of adhesion promoter is strongly dependent on the measurand sensitive material in use. Measurand sensitive layer 20 is typically two to ten microns thick and can be applied in any conventional manner, including spin coating, spray coating, and laminating. In one embodiment, the mixtures of the above examples are spin coated on the polished fiber blocks before being allowed to crosslink.

The well-known Fickian and Case-II swelling manifest themselves as follows on the measurand sensitive layer on the fiber field access block. In Fickian diffusion, the weight, as well as any linear dimension such as the width of the measurand sensitive layer, changes in proportion to $T^{\frac{1}{2}}$, where T represents the time that the sensor has been present in the test chamber. In this case there is a gradient of concentration in absorbed volume. This Fickian diffusion is the normal, expected mode of diffusion. In Case-II swelling, the parameters vary in proportion to T, and there is a uniform concentration of analyte in absorbed volume. This essentially constitutes an abnormal diffusion. As the crosslinking densities are varied, the resulting behavior can be described as a function of time:

$$d \text{ is proportional to } T^\alpha, \alpha=\alpha(p_x), 1 \geq \alpha \geq \tfrac{1}{2}.$$

In this equation, d represents either the thickness t or the weight of layer 20, and the exponent $\alpha$ is a function of the crosslinking density $p_x$. The dynamic behavior of the polymer can thus be changed by varying the crosslinking density $p_x$ as described in the examples above.

Linear non-crosslinked polymers can either enter into solution, remain unaffected, or swell, depending on the physical characteristics of the solvent with which these polymers are in contact. In the case of methyl, ethyl, n-propyl, and iso-butyl alcohols, a special linear non-crosslinked polymer matrix such as poly(methyl methacrylate) can be used as the sensing polymer to detect these analytes without the need for crosslinking, because poly(methyl methacrylate) has a long chain that is capable of functioning in a similar manner as a crosslink.

Although the measurand sensitive layer has been discussed in the context of polymer layers, the material of layer 20 is not limited to polymers. Any material which swells and has an index of refraction different from the index of refraction of glass can be used for layer 20 in the present invention. Examples include metals, such as gold, semiconductors such as silicon, and soft materials such as magnesium oxide. For detection of gasses or heavy metal vapors, metal layers (such as Au for the detection of Hg, Ni for the detection of $O_2$, and palladium for the detection of $H_2$) are used as the measurand sensitive material.

Mechanically, a non-corrugated analyte sensitive layer is equivalent to an elastic material constrained in the plane of the rigid top surface of the fiber field access block. The stress-strain relationship, as described in I. S. Sokolnicoff, *Mathematical Theory of Elasticity*, chapters 3 and 5 (McGraw Hill, N.Y. 1956), can be used to show that, when the layer swells, (a) the stress perpendicular to the layer is zero because the upper surface is not constricted and (b) the strain in the perpendicular direction depends strongly on Poisson's ratio for the sensitive layer and the volume fraction of analyte in the swollen layer. For polymeric non-corrugated layers, the Flory-Huggins theory (see, U. Eisele, *Introduction to Polymer Physics*, pp. 161–64 (Springer-Verlag Berlin Heidelberg 1990)) and free energy equality can be used to show that the strain mentioned above is proportional to the concentration of the solvent in the environmental matrix. In the case of a corrugated polymer, the stress perpendicular to the layer is still zero. However, the strain in the perpendicular direction as well as the stress in the plane of the layer acquire a periodic relationship due to the corrugation.

Various options exist for forming corrugations on a measurand sensitive layer. In one embodiment, a layer of photoresist is applied over the measurand sensitive layer, exposed in selected areas, and developed so as to leave grooves in predetermined locations. The photoresist then acts as a mask, and the material not covered by photoresist can be chemically etched, plasma etched, or laser ablated. If it is not possible to attack the measurand sensitive layer without simultaneously attacking the photoresist, then a mask of an alternate material, for example a metal such as copper, can be applied prior to the photoresist, be removed in selected locations, and act as a mask for the measurand sensitive layer.

In another embodiment, index of refraction variations are caused without creating physical grooves. Processes for image recording on a deformable photovoltaic thermoplastic medium are described in S. Aftergut, "Deformation Recording Media," Kirk-Othmer: Encyclopedia of Chemical Technology, vol. 7, 3rd ed., 1979, John Wiley & Sons, and J. Gaynor & G. J. Sewell, "Photocharge Process," Photographic Science and Engineering, vol. 11, no. 3, May–June 1967, 204–11. To record a pattern, a layer is exposed to a light image and heated to its flow point. The image can be erased by reheating for longer periods.

Figure 2C:
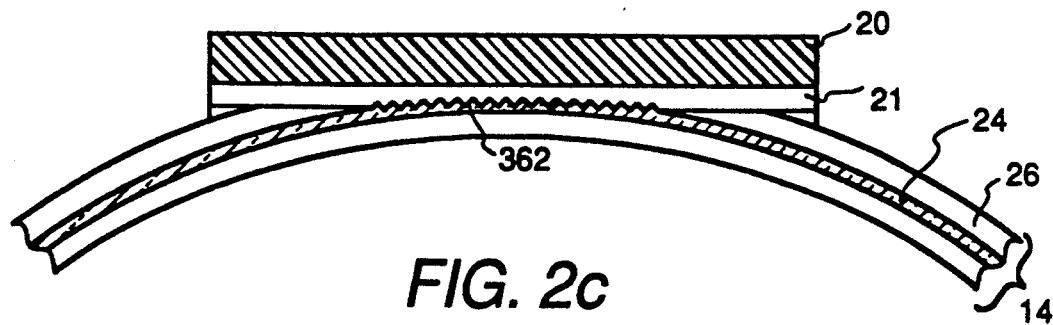
FIG. 2(c) is a sectional side view illustrating an embodiment of the invention wherein the fiber field access block has a corrugated fiber core.

FIG. 2(c) illustrates another embodiment of this environmental sensor which is obtained by using a non-corrugated layer 20 and having a grating with corrugations 362 physically transferred into fiber core 24 by any one of various available techniques, including reactive ion etching, as described in I. Bennion et al., "High Reflectivity Monomode-Fibre Grating Filters," Electronics Letters, Vol. 22, no. 6, pp. 341-43. A thin layer (80-100 nm) of aluminum oxide 21 is deposited over the fiber to provide higher coupling efficiency. The analyte sensitive layer 20 is then deposited or coated on top of this aluminum layer. In this implementation, the sensor is sensitive solely to the index of refraction changes in the sensitive layer.

Figure 2D:
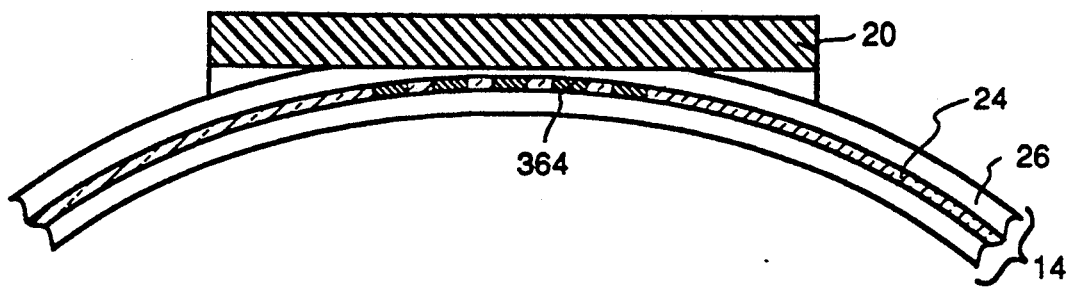
FIG. 2(d) is a sectional side view illustrating another embodiment of the invention wherein the fiber field access block has a corrugated fiber core.

FIG. 2(d) illustrates another embodiment which includes Bragg gratings with optical corrugations 364 formed in the fiber core. These gratings are formed non-invasively by exposing the fiber core, preferably comprising germanosilicate, to an interference pattern of ultraviolet radiation at a wavelength of 244 nm, by a method such as described in G. Meltz et al., "Fiber Bragg Grating Chemical Sensor," SPIE Vol. 1587, pp. 350-61 (1991). The grating is formed after the fiber field access block is polished. The measurand sensitive layer 20 is then coated or deposited on the surface of the fiber field access block. This implementation responds solely to the index of refraction changes in measurand sensitive layer 20.

Figure 3A:
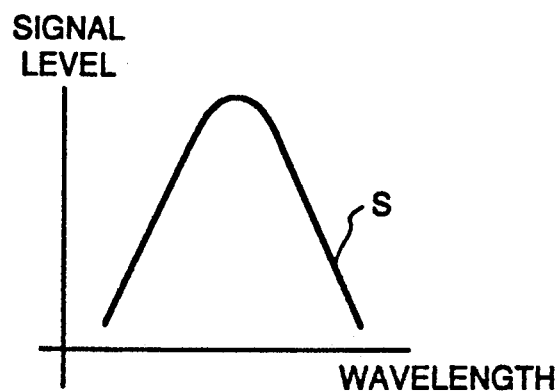
FIG. 3(a) is a graph illustrating an example of an input signal sent into the entrance end of a fiber optic sensor.
Figure 3B:
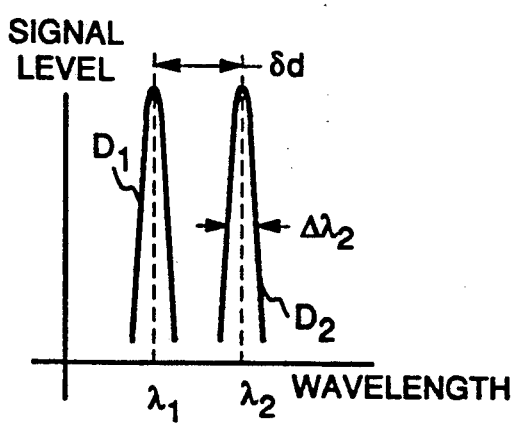
FIG. 3(b) is a graph illustrating an example of a shift in a signal reflected back through the fiber optic sensor of FIG. 2(b)

FIG. 3(a) is a signal level vs. wavelength graph illustrating an example of an input signal S sent into the entrance end of a fiber optic sensor. FIG. 3(b) is a signal level vs. wavelength graph illustrating an example of a shift in signals reflected back through a fiber optic sensor, such as the sensor shown in FIG. 2(b), to optical detection component 12b (FIG. 1). The wavelength of the signal $D_1$ detected under normal conditions (without the effect of the measurand) is represented by $\lambda_1$, whereas $\lambda_2$ represents the wavelength of the signal $D_2$ detected in the presence of the measurand. The shift occurs because of the change in the Bragg condition.

The interaction length L (FIG. 2(a)) affects the width of the reflected peak. As shown in FIG. 3(b), the full width $\Delta\lambda_2$ at half the maximum of the reflected peak is related to the Bragg wavelength (or the center wavelength of the peak) by $$\Delta\lambda_2/\lambda_2 = \Lambda/L,$$

where $\Lambda$ is the period of the grating and L is the interaction length of the fiber. The above equation similarly applies to the peak at wavelength $\lambda_1$.

Figure 3C:
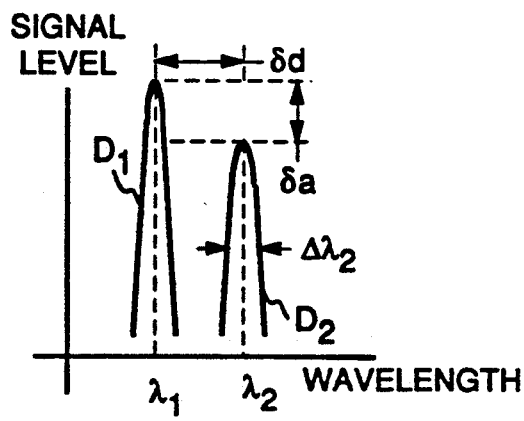
FIG. 3(c) is a graph illustrating an example of a shift in a signal reflected back through the fiber optic sensor of FIG. 2(c)

FIG. 3(c) is a graph illustrating an example of a shift in signals reflected from the measurand sensitive layer back through a sensor of the type shown in FIG. 2(c) to optical detection component 12b (FIG. 1). Unlike the graph of FIG. 3(b), the amplitude of the signal $D_2$ at wavelength $\lambda_2$ is different from the signal $D_1$ at wavelength $\lambda_1$.

Figure 3D:
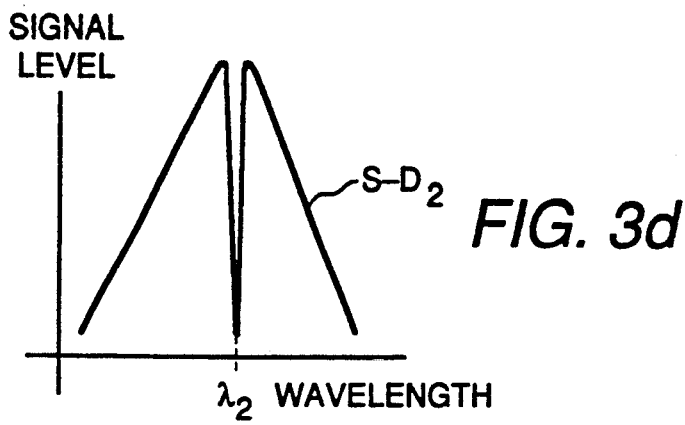
FIG. 3(d) is a graph illustrating an example of an output signal from the exit end of sensor of the invention resulting from detection of a measurand.

FIG. 3(d) is a graph illustrating a signal S-$D_2$ from exit end 14a (FIG. 1) resulting from detection of a measurand, which represents the input signal of FIG. 3(a) minus the reflected signal $D_2$ at wavelength $\lambda_2$ of FIG. 3(b) or FIG. 3(c) at optical detection component 12a (FIG. 1).

Figure 3E:
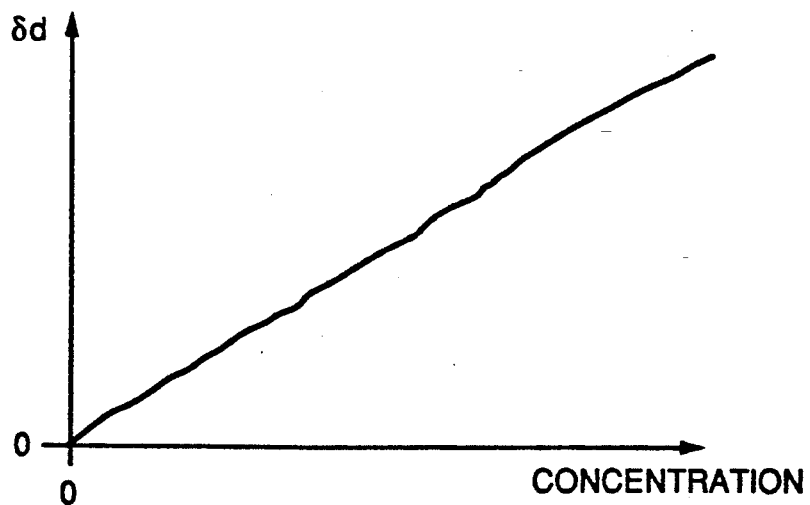
FIG. 3(e) is a graph illustrating a concentration curve for the measurand.

The average concentration of the measurand is determined by measuring the wavelength difference $\delta_d$ (FIG. 3(b) or FIG. 3(c)) or the signal level difference $\delta_a$ (FIG. 3(c)) between the normal signal and the signal in the presence of the measurand. FIG. 3(e) is a graph of a concentration curve which corresponds to $\delta_d$. Data points on the concentration curve are obtained by supplying known concentrations or physical properties and, for each, measuring the respective $\delta_d$. After sufficient data points are obtained, a curve can be interpolated. Ideally the measurand sensitive material, grating period of the corrugations, and crosslinking properties will be selected so as to result in a straight line for the desired measurand, because the more linear the curve, the more precise the measurements. After the curve is graphed, an unknown concentration of a measurand can be determined by measuring the wavelength difference $\delta_d$ and finding the corresponding concentration as indicated on the concentration curve. A similar process can be used to prepare a graph for the signal level difference $\delta_a$ (not shown).

Figure 4:
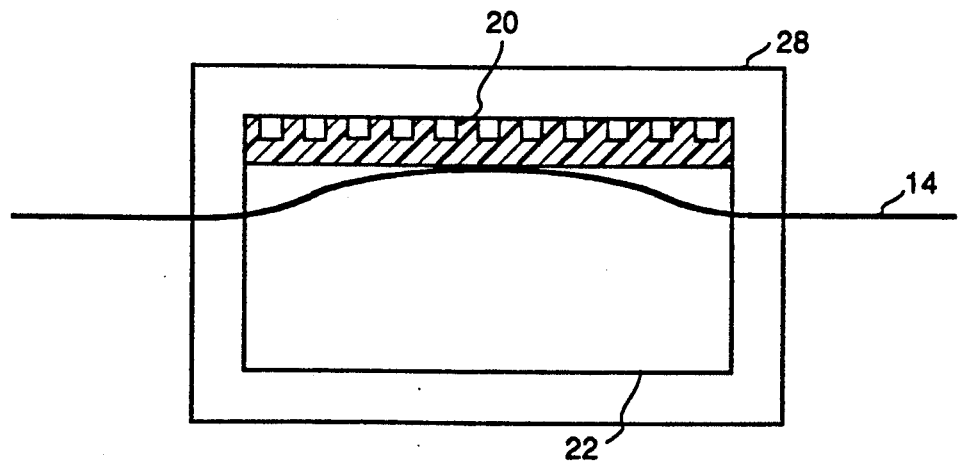
FIG. 4 is a schematic side view of a fiber optic sensor of the invention having an environmental cover.

FIG. 4 is a schematic side view of a fiber optic sensor having an environmental cover 28. The cover, which prevents contamination of the measurand sensitive layer, is useful for isolating a sensor from chemicals and the environment and measuring changes due solely to physical conditions. One example of an appropriate material for cover 28 is Teflon polytetrafluoroethylene, sold by E.I. Dupont de Nemours and Co. With this design, a sensor can be used to sense physical properties such as temperature and pressure without being affected by properties of the analytes.

Figure 5A:
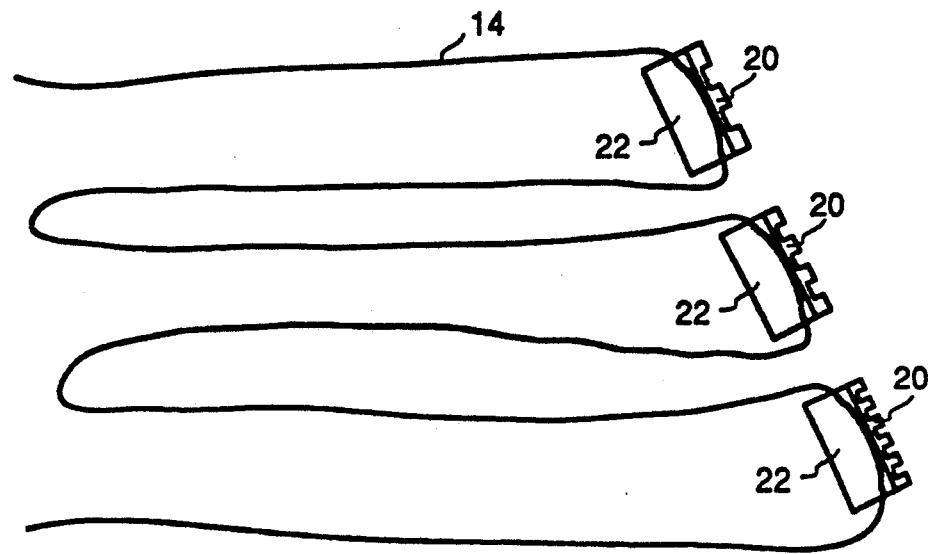
FIG. 5(a) is a schematic side view of three fiber optic sensors of the invention coupled in series.

FIG. 5(a) is a schematic side view of three fiber optic sensors coupled in series. An advantage of coupling the fiber optic sensors is that only one set of optical source and optical detection component (not shown) is needed. Another advantage is that a fiber optic sensor can have a cover 28 (shown and discussed with respect to the embodiment of FIG. 4) which can be used to detect physical conditions and then compared with the signals of the other sensor or sensors, thus allowing analyte measurement which is not affected by changes in physical conditions.

Although fiber 14 is represented in FIGS. 5(a)-5(d) as being a continuous fiber, it is easier to fabricate the design by using a separate fiber for each sensor and fusing the separate fibers together. Moreover, although FIGS. 5(a)-5(d) show embodiments having corrugated measurand sensitive layers 20, the discussion is equally applicable to non-corrugated measurand sensitive layers overlying corrugated fibers except that the grating period of interest is that of the fiber and not the measurand sensitive layer.

Coupling in series can be accomplished, for example, by wavelength division multiplexing. For wavelength division multiplexing, each sensor is assigned a nonoverlapping wavelength range. One optical signal is supplied from the optical source to the sensors. Several methods are available for providing separate sensors with separate wavelength ranges. The method illustrated in FIG. 5(a) is that of using a different grating period for each sensor. This period of the grating has a direct effect on which wavelengths can be reflected, and thus on which wavelengths will be transmitted through the fiber. An optical detection component (such as component 12a shown in FIG. 1) then demultiplexes (separates) the combined optical signals.

Figure 5B:
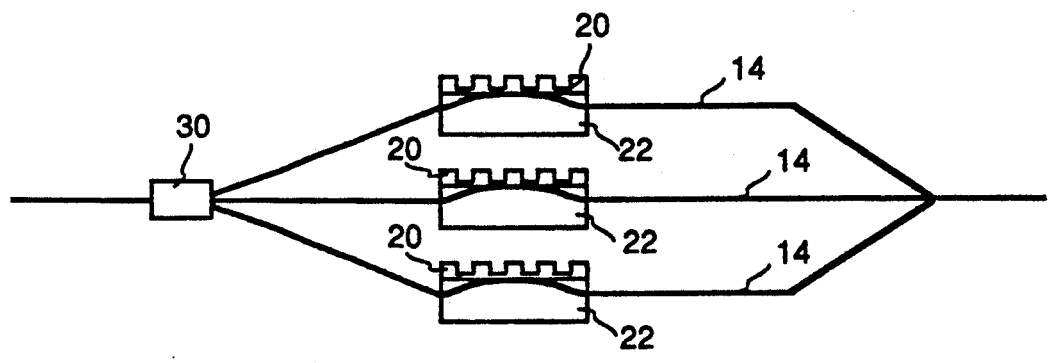
FIG. 5(b) is a schematic side view of three fiber optic sensors of the invention coupled in parallel.

FIG. 5(b) is a schematic side view of three fiber optic sensors coupled in parallel. A conventional time division or wavelength division multiplexer 30 can be used with this embodiment of the present invention. Or, as discussed with respect to the embodiments of FIGS. 5(a), 5(c), and 5(d), grating period, exposed fiber length, measurand sensitive material, or crosslinking density variations can be used for multiplexing.

Figure 5C:
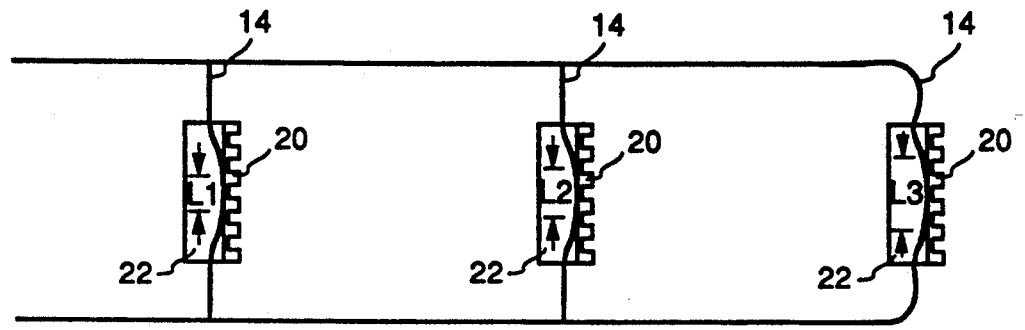
FIG. 5(c) is a schematic side view of three fiber optic sensors of the invention coupled in a ladder pattern.

FIG. 5(c) is a schematic side view of three fiber optic sensors coupled in a ladder pattern. The coupling is parallel, like the design of the embodiment of FIG. 5(b), but because the lengths between each sensor and the source and detection component (not shown) are different, time division multiplexing is easily achieved without need for a time division multiplexer. Additionally, in the embodiment of FIG. 5(c) there are different lengths (L1, L2, L3) of fiber exposed to measured sensitive layers 20. This factor can be used for wavelength division multiplexing because the varying lengths of fiber exposed to layer 20 affect the wavelengths at which a signal from fiber 14 will interact with layer 20.

Figure 5D:
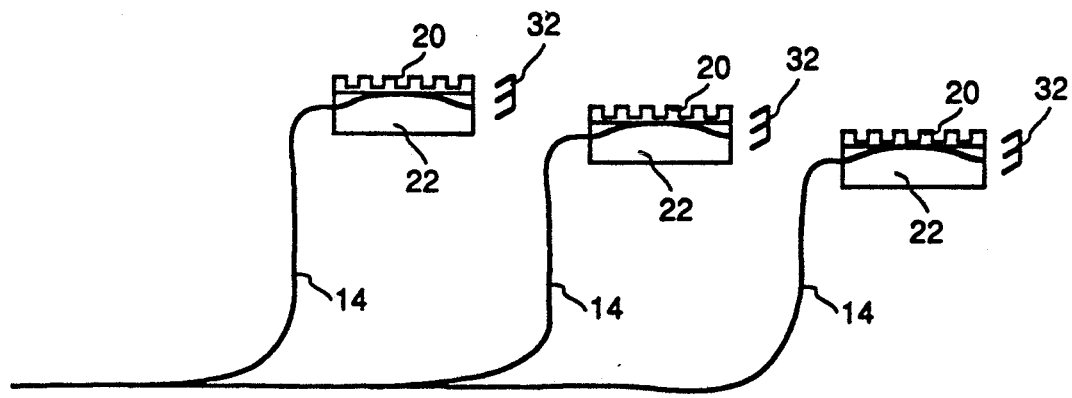
FIG. 5(d) is a schematic side view of three fiber optic sensors of the invention coupled in a reflective pattern.

FIG. 5(d) is a schematic side view of three fiber optic sensors coupled in a reflective pattern to reflectors 32. As in the embodiment of FIG. 5(c), the fiber lengths between the sensors and the source and detection component are different so time division multiplexing is available. One beneficial distinction of the configuration of FIG. 5(d) is that sensitivity is improved because the signal passes through the fiber optic sensor twice, once before reflection and once after reflection.

Even if the lengths of fibers and grating periods were the same, wave division multiplexing can be achieved by using different measurand sensitive materials (which thus have different indices of refraction) or by using different degrees of crosslinking, both of which affect the wavelengths at which a signal from fiber 14 will interact with layer 20.

Another option is to use a combination of the variables of grating period, exposed fiber length, measurand sensitive layer material, the degree of crosslinking. When determining these variables, the nature of the measurand must be considered. In the preferred embodiment, the variables are chosen so that the concentration curve (shown in FIG. 3(e)) is as linear as possible.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. An apparatus for detecting presence of a measurand, comprising:
   a fiber field access block;
   a corrugated measurand sensitive layer over said fiber field access block; and
   means for detecting changes in a parameter selected from the group of thickness and index of refraction of said measurand sensitive layer caused by interaction with said measurand; and
   wherein said fiber field access block has a clad fiber positioned such that a portion of said clad fiber is exposed to said measurand sensitive layer and any cladding on said portion of said clad fiber is thinner than required to prevent an evanescent wave from escaping said clad fiber.

2. The apparatus of claim 1, wherein said corrugated measurand sensitive layer comprises one of the group consisting of physical and optical corrugations.

3. The apparatus of claim 1, wherein said measurand sensitive layer comprises a crosslinked polymer.

4. The apparatus of claim 3, wherein said crosslinked polymer layer comprises one of the group consisting of poly(chloroprene), styrene-butadiene-styrene copolymer, gelatin, and diethylene triamene.

5. The apparatus of claim 1, wherein said measurand sensitive layer comprises a linear non-crosslinked polymer.

6. The apparatus of claim 5, wherein said non-crosslinked polymer comprises polymethylmethacrylate.

7. The apparatus of claim 1, wherein said measurand sensitive layer comprises material selected from the group consisting of metal, silicon, and magnesium oxide.

8. The apparatus of claim 1, further including:
   an optical source coupled to one end of said clad fiber;
   a directional fiber;
   a directional coupler coupling said directional fiber to the portion of said clad fiber situated between said optical source and said fiber field access block; and
   an optical detection component coupled to said directional fiber for measuring reflections from said corrugated measurand sensitive layer into said clad fiber.

9. The apparatus of claim 1, further including:
   an optical source coupled to one end of said clad fiber; and
   an optical detection component coupled to the other end of said clad fiber.

10. The apparatus of claim 1, further including a cover enclosing said measurand sensitive layer for preventing contamination of said measurand sensitive layer.

11. The apparatus of claim 1, wherein said fiber field access block and said measurand sensitive layer comprise a first fiber field access block and a first measurand sensitive layer, respectively, and further comprising:
   a second fiber field access block; and
   a second corrugated measurand sensitive layer overlying said second fiber field access block;
   wherein said second fiber field access block has a second clad fiber positioned such that a portion of said second fiber is exposed to said second measurand sensitive layer and any cladding on said portion of said second fiber is thinner than required to prevent an evanescent wave from escaping said second fiber;
   wherein said first fiber field access block and said second fiber field access block are optically coupled together; and
   wherein said first fiber field access block and said first measurand sensitive layer differ from said second fiber field access block and said second measurand sensitive layer in a feature selected from the group consisting of length of portion of fiber exposed to said measurand sensitive layer, material, degree of crosslinking, and period of grating of corrugations of said measurand sensitive layer.

12. The apparatus of claim 11, wherein said first and second fiber field access blocks are optically coupled together in one configuration of the group consisting of series, parallel, ladder, and reflective.

13. The apparatus of claim 1, wherein said fiber field access block and said measurand sensitive layer comprise a first fiber field access block and a first measurand sensitive layer, respectively, and further comprising:
   a second fiber field access block; and
   a second corrugated measurand sensitive layer overlying said second fiber field access block;
   wherein said second fiber field access block has said clad fiber positioned such that a portion of said clad fiber is exposed to said second measurand sensitive layer and any cladding on said portion of said clad fiber is thinner than required to prevent an evanescent wave from escaping said clad fiber; and wherein said first fiber field access block and said first measurand sensitive layer differ from said second fiber field access block and said second measurand sensitive layer in a feature selected from the group consisting of length of portion of fiber exposed to said measurand sensitive layer, material, degree of crosslinking, and period of grating of corrugations of said measurand sensitive layer.

14. An apparatus for detecting presence of a measurand, comprising:
   a fiber field access block;
   a measurand sensitive layer over said fiber field access block; and
   means for detecting changes in a parameter selected from the group of thickness and index of refraction of said measurand sensitive layer caused by interaction with said measurand;
   wherein said fiber field access block has a clad corrugated fiber positioned such that a portion of said corrugated fiber is exposed to said measurand sensitive layer and any cladding on said portion of said corrugated fiber is thinner than required to prevent an evanescent wave from escaping said corrugated fiber.

15. The apparatus of claim 14, wherein said corrugated fiber comprises one of the group consisting of physically corrugated fiber and optically corrugated fiber.

16. The apparatus of claim 14, wherein said measurand sensitive layer is selected from the group consisting of crosslinked polymers, linear uncrossed polymers, metals, silicon, magnesium oxide, and gold.

17. The apparatus of claim 14, further including:
   an optical source coupled to one end of said corrugated fiber;
   a directional fiber;
   a directional coupler coupling said directional fiber to the portion of said corrugated fiber situated between said optical source and said fiber field access block; and
   an optical detection component coupled to said directional fiber for measuring reflections from said measurand sensitive layer into said corrugated fiber.

18. The apparatus of claim 14, further including:
   an optical source coupled to one end of said corrugated fiber; and
   an optical detection component coupled to the other end of said corrugated fiber capable of measuring spectral shifts in the output signal caused by variations in reflections off said measurand sensitive layer into said corrugated fiber.

19. The apparatus of claim 14, further including a cover enclosing said measurand sensitive layer for preventing contamination of said measurand sensitive layer.

20. The apparatus of claim 14, wherein said fiber field access block and said measurand sensitive layer comprise a first fiber field access block and a first measurand sensitive layer, respectively, and further comprising:
   a second fiber field access block; and
   a second measurand sensitive layer overlying said second fiber field access block;
   wherein said second fiber field access block has a second corrugated fiber positioned such that a portion of said second corrugated fiber is exposed to said second measurand sensitive layer and any cladding on said portion of said second corrugated fiber is thinner than required to prevent an evanescent wave from escaping said second corrugated fiber;
   wherein said first fiber field access block and said second fiber field access block are optically coupled together; and
   wherein said first fiber field access block and said first measurand sensitive layer differ from said second fiber field access block and said second measurand sensitive layer in a feature selected from the group consisting of length of portion of fiber exposed to said measurand sensitive layer, period of grating of corrugations of said corrugated fiber, material and degree of crosslinking of said measurand sensitive layer.

21. The apparatus of claim 14, wherein said fiber field access block and said measurand sensitive layer comprise a first fiber field access block and a first measurand sensitive layer, respectively, and further comprising:
   a second fiber field access block; and
   a second measurand sensitive layer overlying said second fiber field access block;
   wherein said second fiber field access block has said corrugated fiber positioned such that a portion of said corrugated fiber is exposed to said second measurand sensitive layer and any cladding on said portion of said corrugated fiber is thinner than required to prevent an evanescent wave from escaping said corrugated fiber; and
   wherein said first fiber field access block and said first measurand sensitive layer differ from said second fiber field access block and said second measurand sensitive layer in a feature selected from the group consisting of length of portion of fiber exposed to said measurand sensitive layer, period of grating of corrugations of said corrugated fiber, material and degree of crosslinking of said measurand sensitive layer.

22. A method for detecting a measurand, comprising the steps of:
   providing a fiber field access block having a clad fiber positioned therein such that a portion of said clad fiber is exposed to an outer surface of said fiber field access block and any cladding on said portion of said clad fiber is thinner than required to prevent an evanescent wave from escaping said clad fiber;
   providing a corrugated measurand sensitive layer over said outer surface of said fiber field access block;
   positioning said fiber field access block in an environmental matrix;
   providing an optical signal through said clad fiber; and
   measuring an optical signal produced from said clad fiber.

23. The method of claim 22, wherein said fiber field access block and said measurand sensitive layer comprise a first fiber field access block and a first measurand sensitive layer, respectively, and further comprising, prior to the step of providing said optical signal, the steps of:
   providing a second fiber field access block having a second clad fiber positioned therein such that a portion of said second fiber is exposed to an outer surface of said second fiber field access block and any cladding on said portion of said second fiber is thinner than required to prevent an evanescent wave from escaping said second fiber;

applying a second corrugated measurand sensitive layer overlying said outer surface of said second fiber field access block;

positioning said second fiber field access block in said environmental matrix; and optically coupling said first and second fiber field access blocks; and wherein said first fiber field access block and said first measurand sensitive layer differ from said second fiber field access block and said second measurand sensitive layer in a feature selected from the group consisting of length of portion of fiber exposed to said measurand sensitive layer, material, degree of crosslinking, and period of grating of corrugations of said measurand sensitive layer.

24. The method of claim 23, wherein said first and second fiber field access blocks are optically coupled together in one configuration selected from the group consisting of series, parallel, ladder, and reflective.

25. The method of claim 23, further including the steps of:

enclosing one of said first and second fiber field access blocks with a cover for preventing contamination prior to providing said optical signal;

measuring the optical signal produced from said second fiber after providing said optical signal; and comparing the optical signals produced by said first and second fibers.

26. The method of claim 22, wherein said fiber field access block and said measurand sensitive layer comprise a first fiber field access block and a first measurand sensitive layer, respectively, and further comprising, prior to the step of providing said optical signal, the steps of:

providing a second fiber field access block having said clad fiber positioned in said second fiber field access block such that a portion of said clad fiber is exposed to an outer surface of said second fiber field access block and any cladding on said portion of said clad fiber is thinner than required to prevent an evanescent wave from escaping said clad fiber; and applying a second corrugated measurand sensitive layer overlying said outer surface of said second fiber field access block; and wherein said first fiber field access block and said first measurand sensitive layer differ from said second fiber field access block and said second measurand sensitive layer in a feature selected from the group consisting of length of portion of fiber exposed to said measurand sensitive layer, material, degree of crosslinking, and period of grating of corrugations of said measurand sensitive layer.

27. A method for detecting a measurand, comprising the steps of:

providing a fiber field access block having a clad corrugated fiber positioned therein such that a portion of said corrugated fiber is exposed to an outer surface of said fiber field access block and any cladding on said portion of said corrugated fiber is thinner than required to prevent an evanescent wave from escaping said corrugated fiber;

providing a measurand sensitive layer over said outer surface of said fiber field access block;

positioning said fiber field access block in an environmental matrix;

providing an optical signal through said corrugated fiber; and measuring an optical signal produced from said corrugated fiber.

28. The method of claim 27, wherein said fiber field access block and said measurand sensitive layer comprise a first fiber field access block and a first measurand sensitive layer, respectively, and further comprising, prior to the step of providing said optical signal, the steps of:

providing a second fiber field access block having a second clad fiber positioned therein such that a portion of said second fiber is exposed to an outer surface of said second fiber field access block and any cladding on said portion of said second fiber is thinner than required to prevent an evanescent wave from escaping said second fiber;

applying a second measurand sensitive layer overlying said outer surface of said second fiber field access block;

positioning said second fiber field access block in said environmental matrix; and optically coupling said first and second fiber field access blocks; and wherein said first fiber field access block and said first measurand sensitive layer differ from said second fiber field access block and said second measurand sensitive layer in a feature selected from the group consisting of length of portion of fiber exposed to said measurand sensitive layer, period of grating of corrugations of said corrugated fiber, material and degree of crosslinking of said measurand sensitive layer.

29. The method of claim 27, wherein said fiber field access block and said measurand sensitive layer comprise a first fiber field access block and a first measurand sensitive layer, respectively, and further comprising, prior to the step of providing said optical source, the steps of:

providing a second fiber field access block having said corrugated fiber positioned in said second fiber field access block such that a portion of said corrugated fiber is exposed to an outer surface of said second fiber field access block and any cladding on said portion of said corrugated fiber is thinner than required to prevent an evanescent wave from escaping said corrugated fiber;

applying a second measurand sensitive layer overlying said outer surface of said second fiber field access block;

positioning said second fiber field access block in said environmental matrix; and wherein said first fiber field access block and said first measurand sensitive layer differ from said second fiber field access block and said second measurand sensitive layer in a feature selected from the group consisting of length of portion of fiber exposed to said measurand sensitive layer, period of grating of corrugations of said corrugated fiber, material and degree of crosslinking of said measurand sensitive layer.

* * * * *